United States Patent [19]

Nicoud et al.

[11] Patent Number: 4,622,409

[45] Date of Patent: Nov. 11, 1986

[54] N-(4-NITROPHENYL)-2-(HYDROXYMETHYL)-PYRROLIDINE AND DEUTERATED DERIVATIVES THEREOF

[76] Inventors: Jean-Francois Nicoud, 32, rue de Gometz, 91140 Bures-sur-Yvette; Joseph Zyss, 28, rue Desaix, 75015 Paris, both of France

[21] Appl. No.: 733,420

[22] Filed: May 13, 1985

Related U.S. Application Data

[63] Continuation of Ser. No. 460,773, Jan. 25, 1983, abandoned.

[30] Foreign Application Priority Data

Jan. 26, 1982 [FR] France ................................ 82 01166

[51] Int. Cl.$^4$ ............................................. C07D 207/08
[52] U.S. Cl. ..................................... 548/570; 307/425; 307/427
[58] Field of Search .......................................... 548/570

[56] References Cited

PUBLICATIONS

Oelofsen, et al.; J.A.C.S., 88, No. 18, 9-20-66, pp. 4254–4257.
Oudar, et al.; Optics Comm., 15, No. 2 (1975), pp. 258–262.
Ermakov, et al.; Instruments & Experimental Techn., 22, No. 1, (1979), pp. 202–204.
Smith, et al.; J.A.C.S., 101 (1979), pp. 5186–5193.
Thomas, "Duterium Labeling in Org. Chem.", (1971), p. 431; Appleton Century Crofts, N.Y.
Guthrie, et al.; J.A.C.S., 92 (1970), pp. 4057–4062.

*Primary Examiner*—Joseph Paul Brust

[57] ABSTRACT

The invention relates to novel paranitroaniline derivatives usable in non-linear optics and electrooptics, as well as to the preparation process for the same. These derivatives are in accordance with formula (I):

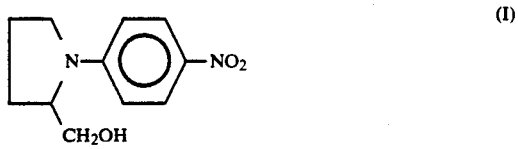

(I)

in which one or more of the hydrogen atoms are optionally replaced by deuterium atoms. They are prepared by reacting one of the two pure optical isomers of 2-(hydroxymethyl)-pyrrolidine with a parahalogenonitrobenzene.

The optically pure derivatives can be used in optical or optoelectronic devices.

2 Claims, No Drawings

N-(4-NITROPHENYL)-2-(HYDROXYMETHYL)-PYRROLIDINE AND DEUTERATED DERIVATIVES THEREOF

This application is a continuation of application Ser. No. 460,773, filed Jan. 25, 1983, now abondaned.

BACKGROUND OF THE INVENTION

The present invention relates to novel paranitroaniline derivatives usable in non-linear optics and in electrooptics, as well as to the preparation process for the same.

The term non-linear optics is understood to mean the field of optics extending from the conversion of optical frequencies (obtaining an optical radiation from two radiations of different frequencies, the frequency of the conversion radiation being equal to the sum or the difference of the frequencies of the two radiations) to electrooptical modulation (modification of one of the characteristics of a radiation by applying an electrical field to a crystal traversed by said radiation).

Numerous materials which are suitable for converting optical frequencies or for electrooptical modulation are already known. The most widely used are frequency doubling crystals based on potassium diphosphate KDP or lithium niobate.

However, these mineral materials have the disadvantage of inadequate efficiency, which makes it necessary to use them in considerable thicknesses. In addition, for a number of years research has been directed at producing crystals of organic molecules having an improved efficiency compared with mineral crystals of potassium diphosphate or lithium niobate. Thus, it has been found that aniline derivatives such as metanitroaniline, 2-methyl-4-nitroaniline, 2-chloro-4-nitroaniline, 2-bromo-4-nitroaniline and methyl-2(2,4-dinitro-phenyl)-aminopropionate can be used for this purpose. It has also been found that pyridine-N-oxide derivatives have interesting properties, one example being 3-methyl-4-nitropyridine-1-oxide (cf "A molecular engineering approach toward the design of efficient organic crystals for three-wave mixing" J. Zyss in Current Trends in Optics, p.122 (Taylor and Francis, London 1981); B. L. Davydov et al ZhETF Pis. Red, 12(1), 24 (1970); and B. F. Levine, C. G. Bethea, C. D. Thurmond, R. T. Lynch and L. Bernstein, J. Appl. Phys. 50, 2523, 1979.

BRIEF SUMMARY OF THE INVENTION

The present invention relates to novel organic compounds derived from paranitroaniline having an improved efficiency in non-linear optics compared with known compounds.

According to a first embodiment of the invention, the paranitroaniline derivative is in accordance with the following formula:

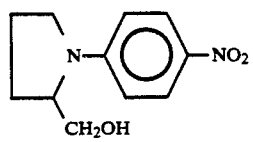

Formula (I)

According to a second embodiment of the invention, the paranitroaniline derivative is in accordance with the above formula (I) in which one or more of the hydrogen atoms are replaced by deuterium atoms.

The paranitroaniline derivative according to formula (I) can be prepared by reacting 2-(hydroxymethyl)-pyrrolidine, commonly called "prolinol" of formula:

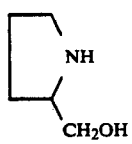

Formula (II)

with a parahalogenonitrobenzene of formula:

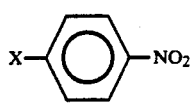

(III)

in which X represents a halogen atom, preferably fluorine, in an appropriate solvent for this type of aromatic nucleophilic substitution. A solvent which can be used is dimethylsulphoxide (DMSO) and dimethylformamide (DMF).

The operating procedure for obtaining this reaction is identical to that described by H. Smith et al J.Am.-Chem.Soc.101, pp.5186–5193 (1979) and H. Bader et al , J. Org. Chem. 31. pp.2319–2321 (1966).

The paranitroaniline derivatives according to formula (I) in which one or more of the hydrogen atoms are replaced by deuterium atoms can be prepared by the partial or total deuteration of the paranitroaniline derivative obtained by reacting 2-(hydroxymethyl)-pyrrolidine of formula (II) with a parahalogenonitrobenzene of formula (III).

This deuteration reaction can be performed by conventional isotopic exchange methods, e.g. by exchange with heavy water $D_2O$, by reaction with DCl and $AlCl_3$, by prolonged treatment in the presence of $D_2SO_4$ or by treatment in deuterated liquid ammonia in the presence of sodamide as the catalyst. These methods are described in "Isotopic exchange and the replacement of hydrogen in organic compounds" (translated from Russian) A.I. SHATENSHTEIN Consultant Bureau N.Y. (1962)–Appendix pp.295–308.

It is also possible to obtain deuterated derivatives of the compound of formula (I) by synthesis by reacting 2-(hydromethyl)-pyrrolidine in partly or totally deuterated form with a parahalogenonitrobenzene of formula (III), which may be deuterated.

The deuterated compounds of formula (II) or formula (III) can be obtained by the aforementioned processes.

The compound of formula (II) used as the starting product for the synthesis of the paranitroaniline derivatives according to the invention can be obtained from L-proline or S-proline, which is a natural amino acid belonging to series L, for which the asymmetrical carbon is of absolute S configuration in accordance with the official nomenclature of organic stereochemistry (cf IUPAC publication, J. Org. Chem. 35, pp.2849–2867 , 1970, Appendix 2). It is therefore possible to directly obtain L-N-(4-nitrophenyl)-2-(hydroxymethyl)-pyrrolidine of formula (I).

However, it is also possible to use in the same way the other non-natural enantiomer or optical isomer of proline belonging to series D for which the asymmetrical carbon is of the absolute R configuration, which makes it possible to directly obtain the present compound of formula (I) with an absolute R configuration and which has the same properties as those of the S derivative in non-linear optics.

When the compound of formula (II) is prepared from non-natural proline, the latter is obtained in racemic form, i.e. an equimolar mixture of the two optical isomers.

In this case, it is possible to cleave or split the racemate by conventional processes in order to use one of the optically pure compounds of formula (II) for preparing the compound of formula (I) according to the invention. However, it is also possible to use the racemate for preparing the compound of formula (I), which is in this case obtained in the form of the racemate, followed by the cleaving of the racemate to obtain the optically pure compounds.

The paranitroaniline derivatives according to the invention, which may or may not be deuterated, have a structure giving them a very high optical non-linearity. Thus, these molecules have a high mobility, asymmetrically delocalized $\pi$ electron system. The presence of an electron acceptor group ($NO_2$) and an electron donor group ($>\ddot{N}-$) linked with the benzene cycle makes it possible to obtain a high conjugation and a charge transfer between the electron donor substituent and the electron acceptor substituent.

Moreover, the fact that the nitrogen atom of the electron donor group is disubstituted makes it possible to make the molecule less sensitive to degradation reactions, which are generally linked with the presence of N—H bonds.

Due to the presence of an asymmetrical S or R carbon in the pyrrolidine cycle, the compounds according to the invention have a non-centrosymmetrical structure making it possible to obtain the non-linearity of the second order.

Moreover, the crystalline structure of the compound according to the invention has optimum characteristics for obtaining non-linear efficiency. Thus, the space group of the crystalline compound is $P2_1$ and the angle of the charge transfer axis connecting the nitrogen of the electron donor group to the nitrogen of the electron acceptor group with the axis of symmetry is 58°, i.e. very close to the optimum theoretical angle of 54°. This makes it possible to improve the non-linear efficiency compared with an identical molecule, whose electron donor and acceptor groups are differently positioned.

In addition, the compounds according to the invention have a consolidated crystalline structure as a result of the presence of an alcohol function, i.e. a polar group in the molecule. In the crystalline structure, these polar groups can establish intermolecular hydrogen bonds, which improve the cohesion.

Thus, when the compounds according to the invention are in crystalline form, the latter have a good mechanical behaviour and have a good resistance to various mechanical treatments and processes, such as cutting and polishing.

Finally, in view of the fact that it is possible to prepare the compounds according to the invention from S(+)2-(hydroxymethyl)-pyrrolidine, which is obtained from natural amino acid and is therefore in an optically pure form, the compounds according to the invention can be directly obtained in the form of optically pure crystals, which obviates the intermediate chemical decomposition or cleavage operations.

When the compound according to the invention of formula (I) is in racemic form, i.e. the equimolar mixture of the two optical isomers, the latter can be crystallized in two forms:

(a) the racemate corresponding to a juxtapositioning of the right and left molecules in the lattice, which leads either to a centrosymmetrical system, or to a non-centrosymmetrical system, but which is at least a mirror system, which is different from that of the optically pure crystal of structure $P2_1$;

(b) the conglomerate corresponding to a juxtapositioning of right and left microcrystals in which case it is possible to obtain a spontaneous cleavage leading to optically pure right or left crystals of structure $P2_1$ (cf A. Collet, M. J. Brienne and J. Jacques, Chemical Reviews, Vol. 80, 3, p.215, 1980).

The compounds according to the invention in the optically pure state can be used in non-linear optics in various forms, e.g. in the form of powders, in the form of inclusions of molecules in a host lattice (polymer, clathrate, solid solution), in the form of thin layers deposited on a substrate, in the form of a monocrystal, in the form of solutions, etc. The compounds according to the invention in the optically pure state can be used in optical or optoelectronic devices using physical effects such as non-linear effects of the first order, i.e. any interaction of three photons in the transparency range of the material e.g. generation of the second harmonic, sum, difference and transposition of frequencies, gain and parametric oscillations, as well as electrooptical effects.

For these various applications, the compounds according to the invention are firstly purified and are then brought into the desired form, e.g monocrystals by conventional processes, e.g. evaporation of the solvent or a growth method in solution by controlled cooling. When it is wished to use them in the form of thin layers, the latter can be produced by the Langmuir-Blodgett method, or by epitaxy.

DESCRIPTION OF PREFERRED EMBODIMENTS

The other characteristics and advantages of the invention can be gathered from the following illustrative and non-limitative description of all embodiments.

This embodiment illustrates the preparation of S(−)N-(4-nitrophenyl)-2-(hydroxymethyl)-pyrrolidine, i.e. the compound according to the invention and the present formula (I).

A first solution is prepared by mixing 25 g (0.25 mole) of S(+)2-(hydroxymethyl)-pyrrolidine or S(+)-prolinol, which is a product produced by ALDRICH, with 25 ml of freshly distilled, anhydrous dimethyl sulphoxide (DMSO).

A second solution is prepared by dissolving 33 g (0.235 mole) of 4-fluoronitrobenzene also produced by ALDRICH in 25 ml of DMSO. The second solution is then poured dropwise into the first solution, accompanied by stirring and cooling on a cold water bath and after adding approximately one equivalent (17 g) of potassium carbonate ($K_2CO_3$). The reaction mixture is then heated at 60° C., whilst continuing stirring. A gaseous emission then occurs, which leads to a large amount of foam and stirring is then continued for 15 hours at 60° C. After cooling, the reaction mixture is poured into 800 ml of ice water, accompanied by vigorous stirring, which is maintained for 1 hour. A yellow precipitate forms, which is filtered on powder glass. The thus separated yellow precipitate is taken up in 500 ml of methylene chloride ($CH_2Cl_2$) until completely dissolved and accompanied by heating, if necessary. The supernatant aqueous phase is allowed to settle and the organic phase is dried with anhydrous magnesium sulphate (MgSO$_4$). After drying, the solvent is evaporated and 48 g of an orange yellow solid is obtained, which corresponds a to yield of 92%.

The product is then purified by recrystallization. For this purpose, the orange yellow product is dissolved in 200 ml of chloroform under heat and reflux, until a homogeneous, clear solution is obtained. This is followed by the dropwise addition of up to 100 ml of very hot cyclohexane until the precipitation limit is reached. Refluxing takes place until a clear solution is obtained and this is followed by recrystallization. In this way, 46 g of crystalline yellow product is obtained having a melting point of 118° C. and a good purity. The overall yield of recrystallized product is 87%. The rotatory power measured in solution in absolute ethanol at a concentration C equal to 1 is:

$[\alpha]_{589}^{18} = -92.1°$ $[\alpha]_{578}^{18} = -97.0°$ $[\alpha]_{546}^{18} = -113.2°$ The space group of the crystalline phase of the product obtained is P2$_1$ and the compound has a crystalline transparency in the range 0.5 to 2 microns. The standard second harmonic generation test performed on the powder of this compound according to the method described in S. K. Kurtz, T. T. Perry, J. Appl. Phys. Vol 39. 8, p.3798, 1958, leads to an efficiency level which is equal to 10$^4$ times that of quartz. A test was carried out using as the source the 1.06 micron line of a YAG: Nd$^{3+}$ laser and by placing the sample at the focus of a parabolic reflector.

The merit criterion (d$^2$/n$^3$) is therefore approximately two orders of magnitude higher than that of lithium niobate.

Thus, this compound has a much higher non-linearity, which is essentially 10 times higher than that of methyl-2-(2,4-dinitrophenyl)-aminopropionate, which is one of the best of the presently known compounds.

What is claimed is:

1. A crystalline paranitroaniline derivative according to the following formula:

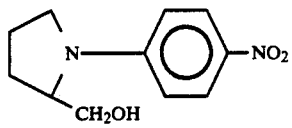

and exhibiting high optoelectronic second order harmonic qualities.

2. A crystalline paranitroaniline derivative having the formula:

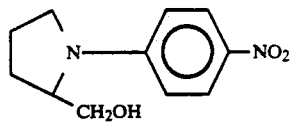

in which at least one of the hydrogen atoms is a deuterated hydrogen atom, said derivative exhibiting high optoelectronic second order harmonic qualitites.

* * * * *